US008882987B2

(12) United States Patent  
Yoshioka et al.

(10) Patent No.: US 8,882,987 B2  
(45) Date of Patent: Nov. 11, 2014

(54) BIOSENSOR MEASUREMENT SYSTEM AND METHOD FOR DETECTING ABNORMAL WAVEFORM IN BIOSENSOR

(75) Inventors: Toshiharu Yoshioka, Ehime (JP); Eriko Yamanishi, Ehime (JP); Hiroyuki Tokunaga, Ehime (JP)

(73) Assignee: Panasonic Healthcare Co., Ltd., Ehime (JP)

( * ) Notice: Subject to any disclaimer, the term of this patent is extended or adjusted under 35 U.S.C. 154(b) by 645 days.

(21) Appl. No.: 12/375,106

(22) PCT Filed: Jul. 26, 2007

(86) PCT No.: PCT/JP2007/064666  
§ 371 (c)(1),  
(2), (4) Date: Jan. 26, 2009

(87) PCT Pub. No.: WO2008/013225  
PCT Pub. Date: Jan. 31, 2008

(65) Prior Publication Data  
US 2009/0205976 A1 Aug. 20, 2009

(30) Foreign Application Priority Data

Jul. 26, 2006 (JP) .................................. 2006-203832

(51) Int. Cl.  
*G01N 33/487* (2006.01)  
*G01N 27/416* (2006.01)  
*G01N 27/327* (2006.01)

(52) U.S. Cl.  
CPC .......... *G01N 27/416* (2013.01); *G01N 27/3271* (2013.01); *G01N 27/3274* (2013.01)  
USPC .............. 205/777.5; 204/403.01; 204/403.02; 204/403.06; 204/403.07; 205/778; 205/792

(58) Field of Classification Search  
CPC ................................. G01N 27/3272  
USPC ............ 204/403.01–403.15; 205/777.5, 778, 205/792  
See application file for complete search history.

(56) References Cited

U.S. PATENT DOCUMENTS 5,352,351 A 10/1994 White et al.  
5,653,863 A 8/1997 Genshaw et al.  
(Continued)

FOREIGN PATENT DOCUMENTS

EP 1 156 324 11/2001  
EP 1 736 763 12/2006  
(Continued)

OTHER PUBLICATIONS

International Search Report issued Oct. 30, 2007 in the International (PCT) Application No. PCT/JP2007/064666.

(Continued)

*Primary Examiner* — Bach Dinh  
(74) *Attorney, Agent, or Firm* — Wenderoth, Lind & Ponack, L.L.P.

(57) ABSTRACT

A biosensor measurement system and a method for detecting abnormal measurement in a biosensor, which can significantly enhance the measurement precision without depending on the user's operation manner or the like, can be provided. A voltage application pattern for applying a voltage to a working electrode, a counter electrode, and a detection electrode has a halt period between a first application period and a second application period, and a reduction current measurement value obtained in the first application period is compared with a reduction current measurement value obtained in the second application period, and the measurement values are not outputted when a difference between the measurement values is outside a predetermined range.

1 Claim, 8 Drawing Sheets

(56) References Cited

U.S. PATENT DOCUMENTS

| | | |
|---|---|---|
| 6,576,117 B1 | 6/2003 | Iketaki et al. |
| 2002/0139692 A1 | 10/2002 | Tokunaga et al. |
| 2004/0154932 A1 | 8/2004 | Deng et al. |
| 2005/0067301 A1 | 3/2005 | Morita et al. |
| 2005/0258034 A1* | 11/2005 | Iketaki et al. ............ 204/403.01 |
| 2006/0037870 A1 | 2/2006 | Deng et al. |

FOREIGN PATENT DOCUMENTS

| | | |
|---|---|---|
| JP | 8-502589 | 3/1996 |
| JP | 8-304340 | 11/1996 |
| JP | 2003-4691 | 1/2003 |
| JP | 2004-245836 | 9/2004 |
| WO | 94/29706 | 12/1994 |
| WO | 99/60391 | 11/1999 |
| WO | 03/044513 | 5/2003 |
| WO | 2005/100968 | 10/2005 |

OTHER PUBLICATIONS

Written Opinion of the ISA issued Oct. 30, 2007 in the International (PCT) Application No. PCT/JP2007/064666.

Extended European Sesarch Report dated Nov. 26, 2013 issued in corresponding European Application No. 07791366.3.

Canadian Office Action mailed Dec. 10, 2013 in corresponding Canadian Patent Application No. 2658920.

* cited by examiner

|  | total | normal | ±30% sensitivity abnormality | judgment possible | judgment impossible |
|---|---|---|---|---|---|
| difference | 1296 | 1223 | 73 | 52 | 21 |
| ratio | 1296 | 1223 | 73 | 3 | 70 |

BIOSENSOR MEASUREMENT SYSTEM AND METHOD FOR DETECTING ABNORMAL WAVEFORM IN BIOSENSOR

TECHNICAL FIELD

The present invention relates to a biosensor measurement system and a method for detecting abnormal waveforms in a biosensor, and more particularly, to those capable of enhancing the measurement precision in the biosensor.

BACKGROUND ART

There has conventionally been a biosensor in which a sample is introduced into a cavity from a front-end suction port by a capillary phenomenon.

Figure 6A:
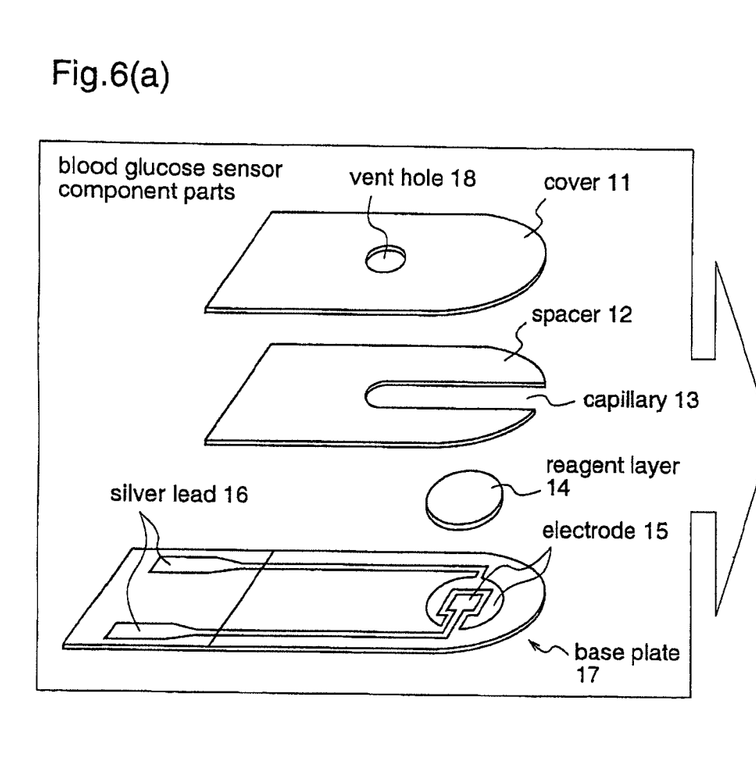
FIG. 6 is a diagram illustrating a biosensor 100 and a measurement device 200 in the biosensor measurement system of the first embodiment.
Figure 6B:
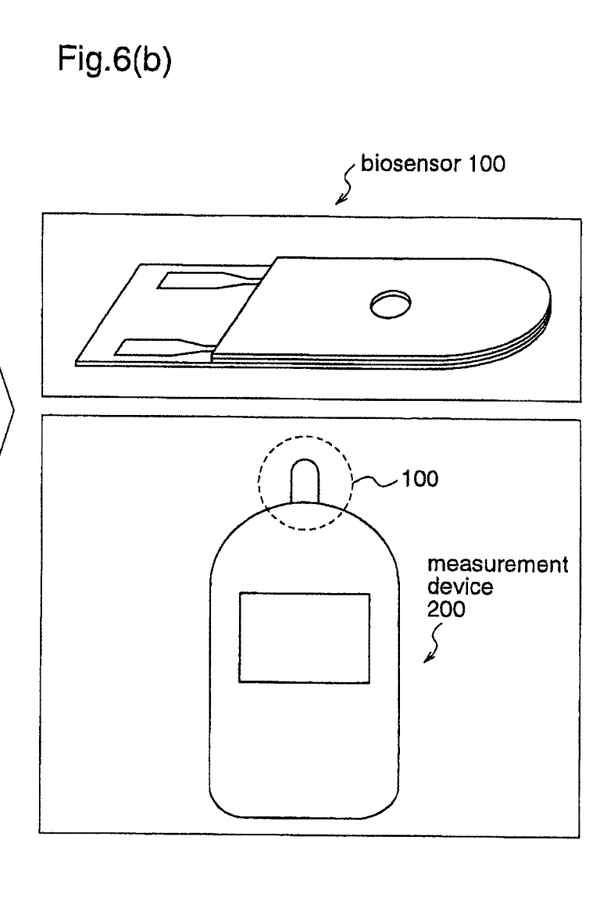

A disposable biosensor 100 shown in FIG. 6(*b*) is detachably attached to a measurement device 200. The biosensor 100 is composed of a cover 11, a spacer 12, and a base plate 17 which are bonded together as shown in an exploded perspective view of FIG. 6(*a*). A sensor electrode 15 on the substrate 17 comprises a working electrode and a counter electrode, and determines the quantity of a base substance by measuring an oxidation or reduction current value which is caused by a voltage applied between the counter electrode and the working electrode. In FIG. 6, reference numeral 13 denotes a capillary for soaking up blood, and reference numeral 18 denotes an air port which enables this soaking-up.

The conventional biosensors as described above have been disclosed in the following documents.

Patent Document 1: Japanese Published Patent Application No. 2004-245836

Patent Document 2: Japanese Published Patent Application No. 2003-4691

Patent Document 3: Japanese Published Patent Application No. Hei. 8-304340

Patent Document 4: International Publication WO 99/60391

Patent Document 5: National Publication of Translated Version No. 8-502589

DISCLOSURE OF THE INVENTION

Problems to be Solved by the Invention

In the respective conventional biosensors described above, if measurement is carried out under the following situations (1) to (4), a higher value or a lower value relative to an appropriate response value might be shown. This results in a deterioration of measurement precision and a reason for market claims.

(1) when the sample is manually supplied in its unstable state,
(2) when the sample is supplied through an unexpected part such as the vent hole,
(3) when the sample in the capillary is scattered or flowed out due to an external factor after starting the measurement,
(4) when sensor malfunction occurs (by such as exposure)

So, a biosensor and a biosensor measurement system which hardly deteriorate the measurement precision even under the above-described situations (1) to (4) have been demanded.

The present invention is made to solve the above-described problems and has for its object to provide a biosensor measurement system which can significantly enhance the measurement precision without depending on the user's operation manner or the like, and a method for detecting measurement abnormality in the biosensor.

Measures to Solve the Problems

In order to solve the above-described problems, according to claim 1 of the present invention, there is provided a method for detecting an abnormal waveform in a biosensor which has at least a working electrode and a counter electrode and measures an oxidation or reduction current value between the working electrode and the counter electrode to determine the quantity of a base substance, wherein a voltage application pattern for applying a voltage between the working electrode and the counter electrode has a halt period between a first application period and a second application period, and the oxidation or reduction current measurement value obtained in the first application period is compared with the oxidation or reduction current measurement value obtained in the second application period, and the measurement values are not outputted when a difference between the measurement values is outside a predetermined range.

According to claim 2 of the present invention, the abnormal waveform detection method defined in claim 1 includes: obtaining P values in formula (1) in the first and second application periods when voltage application is performed according to the voltage application pattern, $$P(t)=X(t)-X(t-\text{const}) \qquad (1)$$

comparing the P value in the first application period with the P value in the second application period, and outputting no measurement values when a difference between the P values is outside a predetermined range.

According to claim 3 of the present invention, the abnormal waveform detection method defined in claim 1 includes: obtaining Q values in formula (2) which are differences in P values in formula (1) in the first and second application periods when voltage application is performed according to the voltage application pattern, $$P(t)=X(t)-X(t-\text{const}) \qquad (1)$$

$$Q(t)=P(t)-P(t-\text{const}) \qquad (2)$$

comparing the Q value in the first application period with the Q value in the second application period, and outputting no measurement values when a difference between the Q values is outside a predetermined range.

According to claim 4 of the present invention, the abnormal waveform detection method defined in claim 1 includes: obtaining P values in formula (3) in the first and second application periods when voltage application is performed according to the voltage application pattern, $$P(t)=X(t)-X\{(T1-T0)(t-T2)/(T3-T2)\} \qquad (3)$$

T0=first application start time
T1=first application end time
T2=second application start time
T3=second application end time comparing the P value in the first application period with the P value in the second application period, and outputting no measurement values when a difference between the P values is outside a predetermined range.

According to claim 5 of the present invention, the abnormal waveform detection method defined in claim 1 includes: obtaining Q values in formula (2) which are differences in P values in formula (3) in the first and second application periods when voltage application is performed according to the voltage application pattern, $$P(t)=X(t)-X\{(T1-T0)(t-T2)/(T3-T2)\} \qquad (3)$$

T0=first application start time
T=first application end time

T2=second application start time
T3=second application end time $$Q(t)=P(t)-P(t-\text{const}) \quad (2)$$

comparing the Q value in the first application period with the Q value in the second application period, and outputting no measurement values when a difference between the Q values is outside a predetermined range.

According to claim 6 of the present invention, there is provided a biosensor measurement system which has at least a working electrode and a counter electrode and measures an oxidation or reduction current value between the working electrode and the counter electrode to determine the quantity of a base substance, and the biosensor measurement system uses a voltage application pattern for applying a voltage between the working electrode and the counter electrode, which pattern has a halt period between a first application period and a second application period, and compares the oxidation or reduction current measurement value obtained in the first application period with the oxidation or reduction current measurement value obtained in the second application period, and outputs no measurement values when a difference between the measurement values is outside a predetermined range.

Effects of the Invention

According to a biosensor measurement system and an abnormal waveform detection method of the present invention which perform measurement using a voltage application pattern having a halt period between a first application period and a second application period, when a normal measurement is carried out, electrons generated by voltage application are consumed and thereby a current response curve of an anterior waveform obtained by the first application and a current response curve of a posterior waveform obtained by the second application transit with constant relation. On the other hand, in the present invention, while the anterior waveform and the posterior waveform deviate from the constant relation to be significantly disordered when an abnormal measurement is carried out, such abnormality is detected by comparing the anterior waveform and the posterior waveform in the above-described situations (1) to (4) such as an impact due to falling of the sensor after starting the measurement, and error display or correction is performed, thereby enhancing the measurement precision.

BRIEF DESCRIPTION OF THE DRAWINGS

FIG. 4 is a diagram illustrating the measured current values which are obtained when performing voltage application with a pattern having a halt period between a first application period and a second application period according to the first embodiment, wherein FIG. 4(a) shows the case where the first application period is equal to the second application period, and FIG. 4(b) shows the case where the first application period is different from the second application period.

DESCRIPTION OF REFERENCE NUMERALS

100 . . . biosensor
200 . . . measurement device
11 . . . cover
12 . . . spacer
13 . . . capillary
14 . . . reagent layer
15 . . . electrode
16 . . . silver lead
17 . . . base plate

BEST MODE TO EXECUTE THE INVENTION

Hereinafter, an embodiment of the present invention will be described with reference to the drawings.
(Embodiment 1)
Hereinafter, a biosensor measurement system and a method for detecting abnormal waveforms in a biosensor according to a first embodiment of the present invention will be described. In this first embodiment, a blood glucose level measurement system using blood as a sample will be described.

Figure 1:
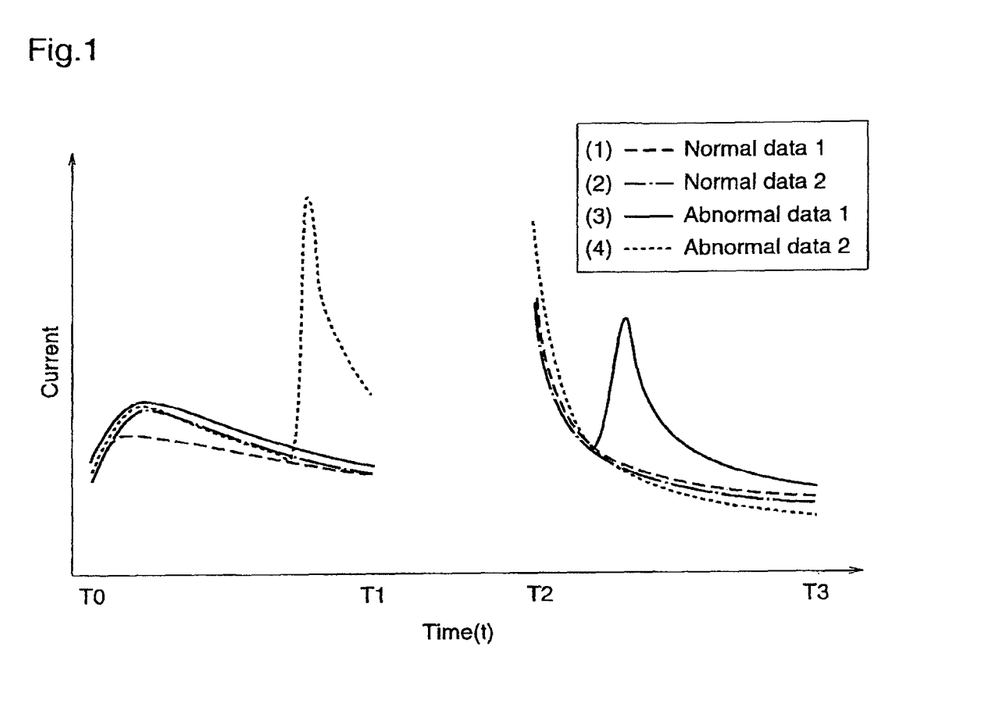
FIG. 1 is a diagram illustrating the results of measured current values of oxidation current which are obtained when performing voltage application with a predetermined voltage application pattern in a biosensor measurement system according to a first embodiment of the present invention.

FIG. 1 is a diagram illustrating the results of measured current values of oxidation or reduction current which are obtained when a voltage is applied to a target substance detection electrode comprising at least a working electrode and a counter electrode, using a voltage application pattern having a halt period T1-T2 between a first application period T0-T1 and a second application period T2-T3 in the biosensor measurement system of this first embodiment, wherein (1), (2), (3), and (4) show Normal data 1, Normal data 2, Abnormal data 1, and Abnormal data 2, respectively.

In the examples of current waveforms shown in FIG. 1, the quantity of glucose is 100 mg/dl and Hct is 45%.

As shown in FIG. 1, when a difference between the anterior waveform and the posterior waveform is taken with respect to Abnormal data 1 and Abnormal data 2, it significantly deviates from the value of Normal data 1 and Normal data 2, and therefore, these Abnormal data 1 and Abnormal data 2 can be eliminated from the normal output.

Figure 2:
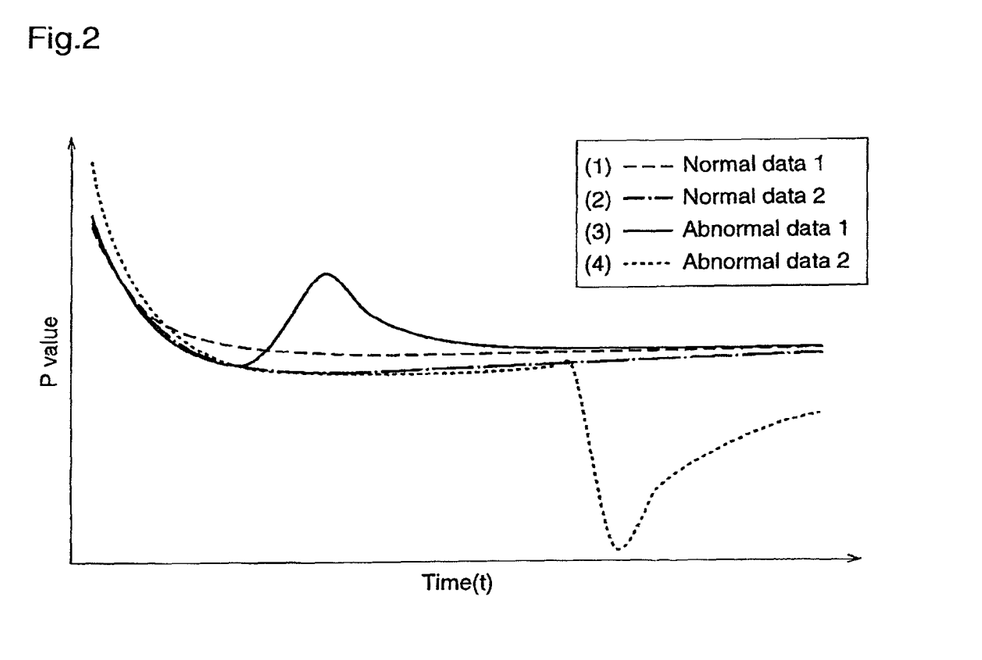
FIG. 2 is a diagram illustrating the calculated results of P values in formula (1) which are obtained when performing voltage application with the predetermined voltage application pattern in the biosensor measurement system of the first embodiment.

FIG. 2 is a diagram illustrating the results obtained by calculating P values in the following formula (1) from the measured current values shown in FIG. 1 in the biosensor measurement system of this first embodiment, wherein (1), (2), (3), and (4) show Normal data 1, Normal data 2, Abnormal data 1, and Abnormal data 2, respectively, as those shown in FIG. 1.

$$P(t)=X(t)-X(t-\text{const}) \tag{1}$$

With reference to FIG. 2, while the P values in Normal data 1 and Normal data 2 vary with a constant relation, the P value in Abnormal data 1 has a peak at the forward side and the P value in Abnormal data 2 has a trough at the backward side, and thereby it is found that the curves of Abnormal data 1 and Abnormal data 2 must be eliminated as the measurement result data.

Figure 5A:
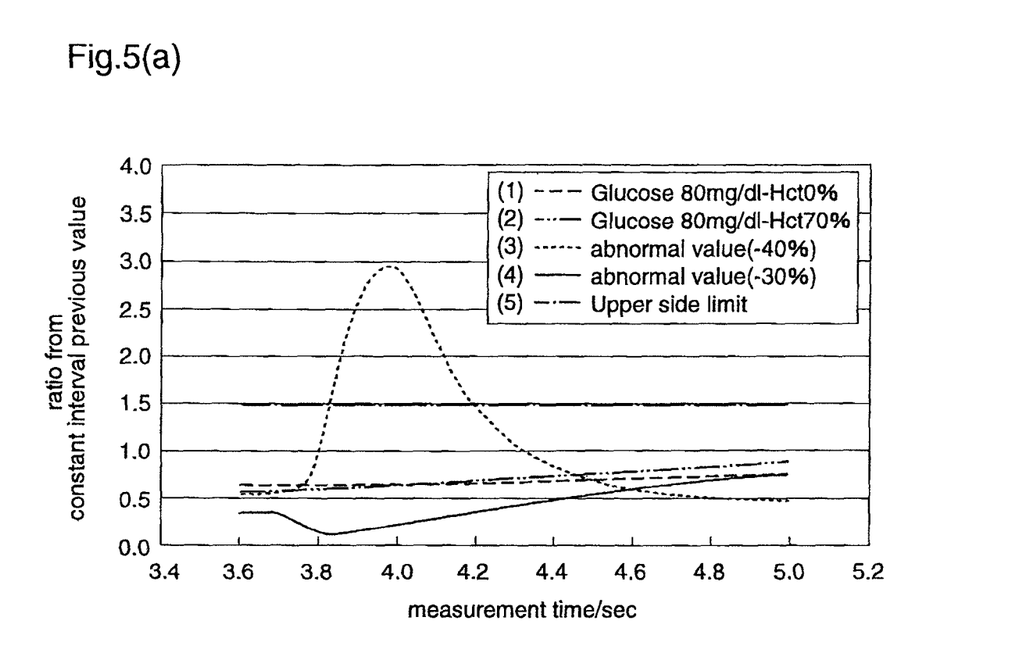
FIG. 5(a) is a diagram illustrating ratio calculation from predetermined period previous measurement values according to the conventional method.
Figure 5B:
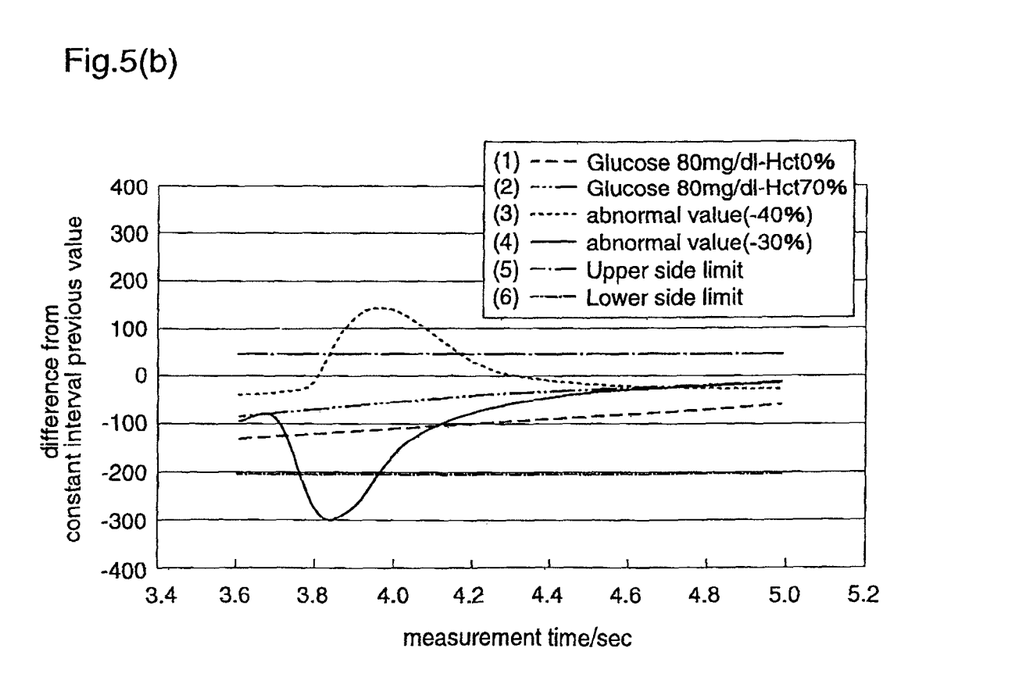
FIG. 5(b) is a diagram illustrating difference calculation from predetermined period previous measurement values according to the first embodiment.
Figure 8:
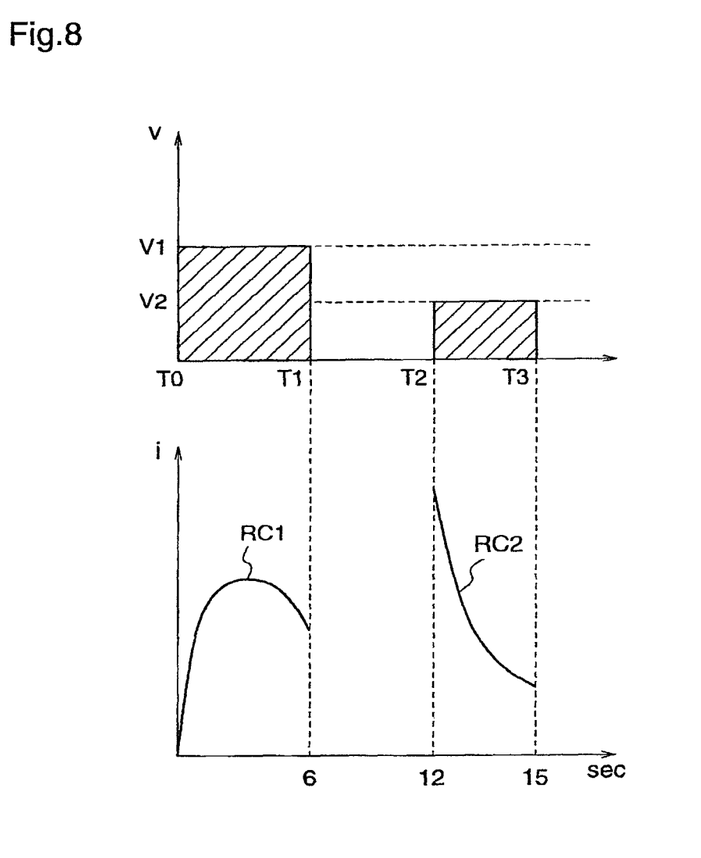
FIG. 8 is a diagram illustrating a voltage application pattern as a measurement algorithm used for the biosensor measurement system of the present invention, and variations in the amount of current upon the voltage application.

Accordingly, in this first embodiment, voltage application is carried out with the voltage application pattern shown in FIG. 8, and the P value which is a difference between the measured current value in the first application period T0-T1 and the measured current value in the second application period T2-T3 is calculated, and the measured values are not outputted when the P value shown in FIG. 5($b$) is outside of the range between the upper side limit and the lower side limit.

In this first embodiment, the normal values are measured in different conditions (n=10, n is the number of samples) with respect to a supposed variation factor such as a specific blood glucose value or hematocrit value, and a threshold range is set based on the values of ±6 SD (standard variation) from the average value −74.8, i.e., ±125.2. That is, the threshold range is set to ±6 SD by statistically estimating the variations in the normal values due to the conditions in order to further enhance the judgment precision.

Figure 3:
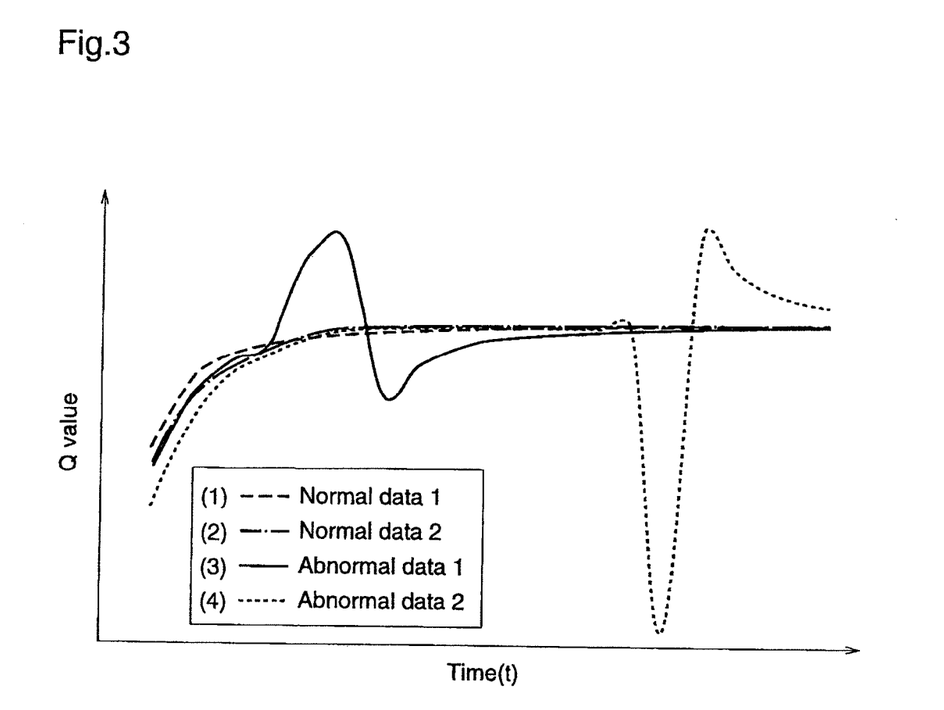
FIG. 3 is a diagram illustrating the calculated results of Q values in formula (2) which are obtained when performing voltage application with the predetermined voltage application pattern in the biosensor measurement system of the first embodiment.

FIG. 3 is a diagram illustrating the results obtained by calculating Q values in the following formula 2 from the above-mentioned P values in the biosensor system of this first embodiment, wherein (1),(2),(3), and (4) show Normal data 1, Normal data 2, Abnormal data 1, and Abnormal data 2, respectively, as shown in FIGS. 1 and 2.

$$Q(t)=P(t)-P(t-\text{const}) \tag{2}$$

With reference to FIG. 3, while the Q values vary with a constant relation in Normal data 1 and Normal data 2, the Q value in Abnormal data 1 has a large peak and a small trough at the forward side, and the Q value in Abnormal data 2 has a large trough and a small peak at the backward side, and thus it is found that the curves of Abnormal data 1 and Abnormal data 2 should be excluded as the measurement result data.

Accordingly, in this first embodiment, the Q values are further calculated after the P values are obtained, and the measurement is judged as abnormal when the Q values exceed a predetermined threshold range.

As described above, the judgment precision can be enhanced by combining the Q values and the P values. Further, the judgment precision can be enhanced by adopting the method of judging that the measured values are abnormal values when either of the P values or the Q values are not normal values.

Figure 4A:
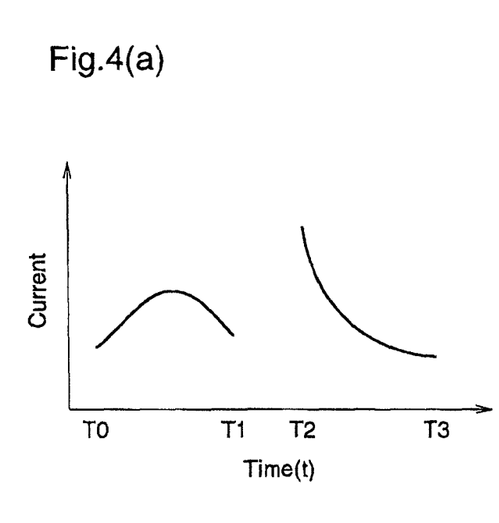
Figure 4B:
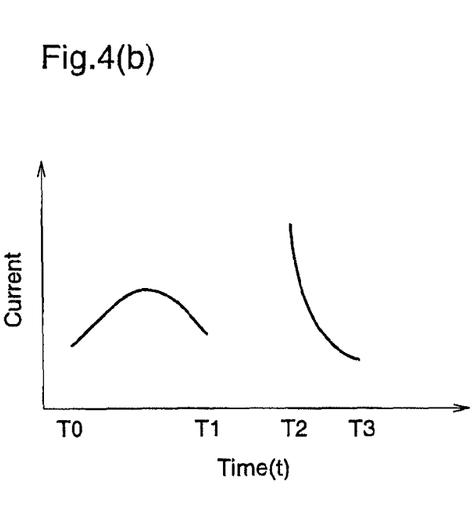

FIGS. 4($a$) and 4($b$) are diagrams illustrating the measured current values obtained when voltage application is performed with a pattern having a halt period between the first application time and the second application time as described above, wherein FIG. 4($a$) shows the case where the first application time (T0-T1) and the second application time (T2-T3) are equal to each other while FIG. 4($b$) shows the case where the first application time (T0-T1) and the second application time (T2-T3) are different from each other.

When the voltage application pattern is as shown in FIG. 4($a$), differences in the measured current values may be simply calculated at constant time intervals (1 sec. between the prior application and the subsequent application). However, when the voltage application pattern is as shown in FIG. 4($b$), P values are calculated using formula 3.

$$P(t)=X(t)-X\{(T1-T0)(t-T2)/(T3-T2)\} \tag{3}$$

T0=first application start time
T1=first application end time
T2=second application start time
T3=second application end time FIG. 5($a$) shows ratio calculation from the constant interval previous measurement value (calculation result obtained by dividing the value at the prior application by the value at the subsequent application with a specific time interval), wherein the abscissa shows time and the ordinate shows the ratio from the constant interval previous value.

In FIG. 5($a$), (1) shows Glucose 80 mg/dl—Hct 0%, (2) shows Glucose 80 mg/dl—Hct 70%, (3) shows abnormal value (31 40%), (4) shows abnormal value (−30%), and (5) shows Upper side limit.

At this time, since Lower side limit must be set within a range close to the normal value, it is difficult to set Lower side limit for avoiding false judgment of the normal value.

On the other hand, FIG. 5($b$) shows different calculation from the constant interval previous measurement value (calculation result of simple difference), wherein the abscissa show the measurement time and the ordinate shows the difference from the constant interval previous value. In FIG. 5($b$), (1) shows Glucose 80 mg/dl—Hct 0%, (2) shows Glucose 80 mg/dl—Hct 70%, (3) shows abnormal value (−40%), (4) shows abnormal value (−30%), (5) shows Upper side limit, and (6) shows Lower side limit. The upper and lower threshold values in this case can be easily set by the same method as described for FIG. 2

Figure 5C:
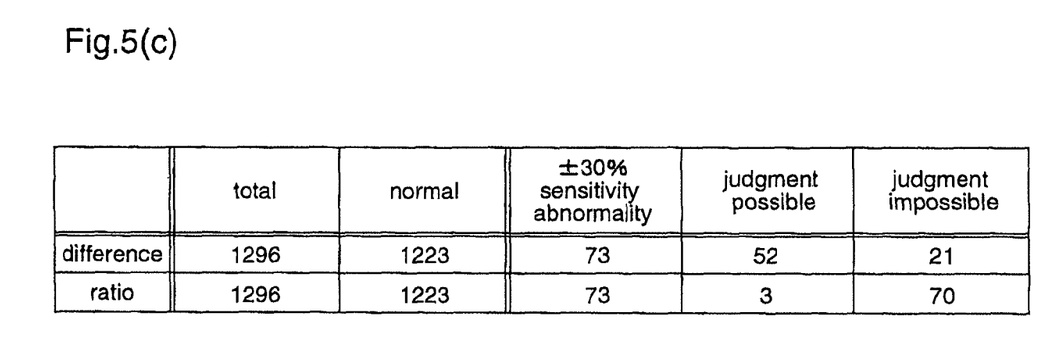
FIG. 5(c) is a diagram illustrating a difference in abnormal detection between the method of the present invention and the conventional method.

FIG. 5($c$) is a table illustrating the judgment results such as defective/non-defective in the case of the above-described difference calculation and ratio calculation of the first embodiment, which are obtained from the results shown in FIGS. 5($a$) and 5($b$), and it is shown in FIG. 5($c$) that the judgment precision by the difference calculation is higher than that by the ratio calculation.

FIG. 6 is a diagram illustrating a biosensor 100 and a measurement device 200 in the biosensor measurement system of this first embodiment, and the biosensor 100 shown in FIG. 6($a$) comprises a cover 11, a spacer 12, a capillary 13, a reagent layer 14, an electrode 15, a silver lead 16, and a base plate 17 which are constituents of a blood glucose sensor.

FIG. 6($b$) shows the manner of applying blood to the biosensor 100 to perform measurement of blood glucose after attaching the biosensor 100 to the measurement device 200.

Figure 7:
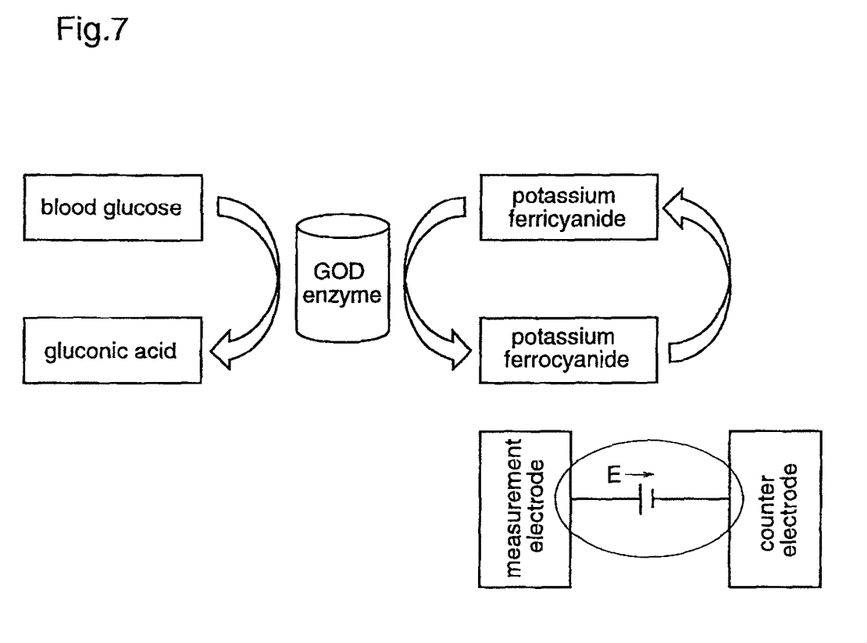
FIG. 7 is a diagram for explaining the measurement principle of the biosensor measurement system of the present invention.

FIG. 7 is a diagram for explaining the measurement principle of the biosensor measurement system having the biosensor 100 and the measurement device 200 of the present invention. When the blood contacts the reagent layer, an enzyme reaction occurs and glucose in the blood reacts with glucose oxidase (GOD enzyme), and simultaneously, potassium ferricyanide in the reagent is reduced to potassium ferrocyanide. The amount of the potassium ferrocyanide generated at this time is in proportion to the glucose concentration. Since electrochemical oxidation occurs when a voltage is applied between the measurement electrode and the counter electrode, the quantity of glucose can be measured by measuring the current at this oxidation, and consequently, the quantity of blood glucose in blood can be detected. The above-described measurement principle can be similarly applied and developed for other enzyme reactions.

FIG. 8 is a diagram illustrating a voltage application pattern as a measurement algorithm in the biosensor of the present invention, and variations in the measured current value with the voltage application.

Although the method itself shown in FIG. 8 is a known method, a voltage application pattern for applying a voltage to a target substance measurement electrode system has a halt period between an anterior first application period and a posterior second application period, and a voltage V1 is applied during the first application period while a voltage V2 is applied during the second application period to obtain reduced currents RC1 and RC2 in the respective application periods. For example, a measured value at the end of the second application period is outputted as such as a blood glucose value as the measurement result.

In this first embodiment, the abnormal measurement result can be eliminated by discriminating the measurement waveform different from the normal measurement waveform, and thereby it is possible to perform error judgment, error display, or correction for all abnormal circumstances which cause waveforms different from the normal measurement waveform, including not only the abnormal values obtained during measurement but also failures (abnormal values) caused by the sensor and the meter.

That is, in all abnormal situations that cause waveforms different from the normal measurement waveform, which are exemplified as follows:

(1) when the sample is manually supplied in its unstable state, (2) when the sample is supplied through an unexpected part such as the vent hole, (3) when the sample in the cavity is scattered or flowed out due to an external factor after starting the measurement, (4) when sensor malfunction occurs (by such as exposure), the above-described difference calculation from the constant interval previous values is carried out to obtain the P values and further the Q values, and the measurement results are eliminated when the values exceed the respective threshold values, whereby only the highly-precise measurement results can be outputted against these situations.

According to the biosensor measurement system and the abnormal waveform detection method of this first embodiment, in the method of detecting an abnormal waveform in a biosensor which has at least a working electrode and a counter electrode and measures an oxidation or reduction current value between the working electrode and the counter electrode to determine the quantity of a base substance, a voltage application pattern for applying a voltage to the working electrode and the counter electrode has a halt period between a first application period and a second application period, and the oxidation or reduction current measurement value obtained in the first application period is compared with the oxidation or reduction current measurement value obtained in the second application period, and the measurement values are not outputted when a difference between the measurement values is outside a predetermined range. Therefore, in the cases where an output of a normal measurement value cannot be expected, such as (1) when the sample is manually supplied in its unstable state, (2) when the sample is supplied through an unexpected part such as the vent hole, (3) when the sample in the cavity is scattered or flowed out due to an external factor after starting the measurement, and (4) when sensor malfunction occurs (by such as exposure), error display is performed and the measured values are not outputted, whereby displays due to incorrect detection results are minimized to significantly enhance the measurement precision of the biosensor.

Applicability In Industry

According to the biosensor measurement system and the abnormal waveform detection method of the present invention, a self blood-glucose measurement biosensor having a high measurement precision can be obtained, which is useful in hospitals and homes.

The invention claimed is:

1. A method comprising detecting an abnormal waveform in a biosensor, which includes at least a working electrode and a counter electrode and measures an oxidation or reduction current value between the working electrode and the counter electrode, to determine a quantity of a base substance, wherein the detecting of the abnormal waveform is performed by applying a voltage between the working electrode and the counter electrode based on a voltage application pattern having a halt period between a first application period and a second application period, comparing the oxidation or reduction current measurement value obtained in the first application period of applying the voltage with the oxidation or reduction current measurement value obtained in the second application period of applying the voltage, and determining that the oxidation or reduction current measurement value obtained in the first application period and the oxidation or reduction current measurement value obtained in the second application period are not output when a difference between the oxidation or reduction current measurement value obtained in the first application period and the oxidation or reduction current measurement value obtained in the second application period is outside a predetermined range;

obtaining P values in formula (1) in the first and second application periods, when the voltage is applied according to the voltage application pattern, $$P(t)=X(t)-X(t-\text{const}) \quad (1),$$

wherein , t represents time,

T0=first application period start time,

T1=first application period end time,

T2=second application period start time,

T3=second application period end time,

X(t) is a measured current value in the second application period ranging from T2 to T3 when the time t ranges within the second application period, X(t−const) is a measured current value in the first application period ranging from T0 to T1, and const represents a time difference between the second application period start time T2 and the first application period start time T0;

comparing the X(t−const) in the first application period with the X(t) in the second application period; and outputting no measurement values when a difference P value between the X(t−const) and X(t) is outside a predetermined range.

* * * * *